United States Patent
Coffman et al.

(10) Patent No.: US 10,508,977 B2
(45) Date of Patent: Dec. 17, 2019

(54) WASH SOLUTION AND METHOD TO REMEDIATE LUBRICANT CONTAMINATION

(71) Applicant: Hologic, Inc., Bedford, MA (US)

(72) Inventors: Erin Coffman, Nashua, NH (US); Steven Hecht, Boston, MA (US); Paul MacLean, Westborough, MA (US)

(73) Assignee: HOLOGIC, INC., Marlborough, MA (US)

( * ) Notice: Subject to any disclaimer, the term of this patent is extended or adjusted under 35 U.S.C. 154(b) by 0 days.

(21) Appl. No.: 15/357,872

(22) Filed: Nov. 21, 2016

(65) Prior Publication Data

US 2018/0143114 A1    May 24, 2018

(51) Int. Cl.
| | |
|---|---|
| *G01N 1/34* | (2006.01) |
| *A01N 1/00* | (2006.01) |
| *G01N 1/28* | (2006.01) |
| *C12N 5/071* | (2010.01) |
| *C08L 33/08* | (2006.01) |
| *C12N 5/00* | (2006.01) |

(52) U.S. Cl.
CPC .............. *G01N 1/34* (2013.01); *A01N 1/00* (2013.01); *C12N 5/0682* (2013.01); *G01N 1/286* (2013.01); *C08L 33/08* (2013.01); *C12N 5/00* (2013.01)

(58) Field of Classification Search
CPC .......... G01N 1/34; G01N 1/286; C08L 33/08; C12N 5/00; C12N 5/0682; A01N 1/00
See application file for complete search history.

(56) References Cited

U.S. PATENT DOCUMENTS

| | | | |
|---|---|---|---|
| 5,269,918 A | 12/1993 | Lapidus et al. | |
| 5,282,978 A | 2/1994 | Polk, Jr. et al. | |
| 6,562,299 B1 | 5/2003 | Ostgaard et al. | |
| 6,572,824 B1 | 6/2003 | Ostgaard et al. | |
| 6,657,003 B2 * | 12/2003 | Fox ..................... | C12N 5/0068 435/180 |
| 7,579,190 B2 | 8/2009 | Ostgaard et al. | |
| 2004/0081979 A1 | 4/2004 | Knezevic et al. | |

OTHER PUBLICATIONS

Arfmann et al. Nature of Amino Acid Side Chain and &-Helix Stability. Biopolymers (1975), v14, p. 1381-139 (Year: 1975).*
Buffer Chart. Sigma-Aldrich (2000), 2 pages. (Year: 2000).*
BD SurePath (TM) Preservative Fluid MSDS (2011), 7 pages. (Year: 2011).*
Digene® HC2 High-Risk HPV DNA Test Instructions for Use. Qiagen test kit instructions, Aug. 2015, 128 pages. (Year: 2015).*
PCT International Search Report and Written Opinion dated Mar. 28, 2018 for PCT application No. PCT/US2017/061841, Applicant Hologic, Inc. 19 pages.
PCT invitation to pay additional fees and partial search report dated Feb. 5, 2018 for application No. PCT/US2017/061841, Applicant Hologic, Inc. 15 pages.
Erin Coffman, et al., "Use of a Unique Wash Solution to Remediate Lubricant Contamination from ThinPrep Specimens", Journal of American Society of Cytopathology, 2015, p. S86, [retrieved on Jan. 19, 2018].
Melissa Randolph et al., "Reprocessing unsatisfactory ThinPrep Papnicolaou tests using a modified SurePath preparation technique: Reprocessing Unsatisfactory ThinPrep Test", pp. 343-348, Cancer Cytopathology, May 2014; published online Feb. 20, 2014.
Tim D. Feit et al., "Interference Potential of Personal Lubricants and Vaginal Medications on ThinPrep® Pap Tests", Journal of the American Board of Family Medicine, vol. 24, No. 2, Mar. 2, 2011, pp. 181-186.
Tatyana Kalinicheva, MD, et al., "Etiologic factors related to unsatisfactory ThinPrep® cervical cytology: Evaluation and potential solutions to improve", CytoJournal, Jan. 1, 2015, pp. 1-31.
Nilson B.H.K. et al., : "Protein L from Peptostreptococcus magnus binds to the kappa light chain variable domain", Journal of Biological Chemistry, American Society for Biochemistry and Molecular Biology, vol. 267, No. 4, Feb. 5, 1992, pp. 2234-2239.

* cited by examiner

*Primary Examiner* — Sean C. Barron
(74) *Attorney, Agent, or Firm* — Vista IP Law Group LLP

(57) ABSTRACT

A wash solution for remediating lubricant contamination in cytological specimens includes a Tris-based alkaline buffer solution. The buffer solution may be prepared in methanol, and may include a proton-rich protein, or a basic amino acid, such as arginine, lysine, or guanidine. A method for remediating a specimen contaminated with lubricant includes using the wash solution and/or adding a salt to the final vial prior to preparing the microscope slide. The method may include adding the wash solution to the specimen, centrifuging the specimen and wash solution to form a supernatant and cell pellet, decanting the supernatant, and adding a preservative solution to the cell pellet. The method may further include adding salt to a vial containing the preservative solution and cell pellet.

8 Claims, 5 Drawing Sheets

| | No Treatment | Wash Treatment | Wash + CytoLyt Salts | Total Slides |
|---|---|---|---|---|
| ATR Pool | 0/48 (0%) | 5/39 (12.8%) | 39/43 (90.7%) | 130 |
| LSIL Pool | 0/42 (0%) | 10/39 (25.6%) | 48/48 (100%) | 129 |
| WNL Pool | 0/54 (0%) | 12/42 (28.6%) | 48/48 (100%) | 144 |
| Total Slides | 144 | 120 | 139 | 403 |
| Totals with ≥5000 | 0 (0%) | 27 (22.5%) | 135 (97.1%) | |

| | No Treatment | Wash Treatment | Wash + CytoLyt Salts |
|---|---|---|---|
| SAT | 5 | 24 | 66 |
| SAT - Borderline | 2 | 4 | 5 |
| UNSAT - Borderline | 3 | 8 | 1 |
| UNSAT | 69 | 36 | 0 |
| Totals | 79 | 72 | 72 |
| % UNSAT Rate | 91.1% | 61.1% | 1.4% |

WASH SOLUTION AND METHOD TO REMEDIATE LUBRICANT CONTAMINATION

FIELD

The inventions disclosed herein relate generally to a wash solution and a method, respectfully, for remediating cytological specimens that are contaminated or potentially contaminated with a lubricant.

BACKGROUND

Cytology is a branch of biology dealing with the study of the formation, structure, and function of cells. As applied in a laboratory setting, cytologists, cytotechnologists, and other medical professionals make medical diagnoses of a patient's condition based on visual examination of a specimen of the patient's cells. A typical cytological technique is a "pap" test, in which cells are scraped from a woman's cervix and analyzed in order to detect the presence of abnormal cells, a precursor to the onset of cervical cancer. Cytological techniques are also used to detect abnormal cells and disease in other parts of the human body.

Cytological techniques are widely employed because collection of cell samples for analysis is generally less invasive than traditional surgical pathological procedures such as tissue extraction biopsies. Cell samples may be obtained from the patient by a variety of techniques including, for example, by scraping or swabbing an area, or by using a needle to aspirate body fluids from the chest cavity, bladder, spinal canal, or other appropriate area. The cell samples are placed in solution and subsequently collected and transferred to a glass slide for viewing under magnification. Fixative and staining solutions may be applied to the cells on the glass slide for preserving the specimen for archival purposes and for facilitating examination.

It is generally desirable that the cells on the slide have a proper spatial distribution, so that individual cells can be examined. A single layer of cells is typically preferred. Accordingly, preparing a specimen from a fluid sample containing many cells typically requires that the cells first be separated from each other by mechanical dispersion, fluidic shear, or other techniques so that a thin, monolayer of cells can be collected and deposited on the slide. In this manner, the cytotechnologist can more readily discern abnormal cells. The cells in the monolayer are also able to be counted to ensure that an adequate number of cells have been evaluated.

Certain methods and apparatus for generating a thin monolayer of cells on a slide advantageous for visual examination are disclosed in U.S. Pat. Nos. 5,143,627, 5,240,606, 5,269,918, 5,282,978, 6,572,824, 6,562,299 and 7,579,190, all of which are assigned to the assignee of the present invention, and all of the disclosures of which are incorporated herein by reference in their entirety.

According to one method disclosed in these patents, a patient's cells in a preservative fluid in a sample container are dispersed using a spinning filter device disposed therein. A controlled vacuum is applied to the filter device to draw the fluid through a membrane thereof, until a desired quantity and spatial distribution of cells is collected against the filter. Thereafter, the filter is removed from the sample container and the filter membrane impressed against a glass slide to transfer the particles of interest to the slide in substantially the same spatial distribution as they were collected on the filter membrane.

Once a specimen is prepared, fixed, and stained, the specimen may be manually visually inspected by a cytotechnologist, typically under magnification, and with or without various sources of illumination. Alternatively or additionally, automated machine vision systems have been adapted to aid cytological inspection. For example, an automated vision system may perform a preliminary assessment of the entire slide on which the specimen is disposed to alert the cytotechnologist to potentially the most relevant areas of the slide for close inspection, or may be used to rescreen specimens already analyzed by the cytotechnologist.

The ThinPrep® 2000, ThinPrep® 3000, and ThinPrep® 5000 systems (collectively, "ThinPrep® system"), manufactured and sold by Hologic, Inc. ("Hologic"—formerly Cytyc Corporation), located in Marlborough, Mass., are effective and widely used cervical cancer screening tools available to women. Since the introduction of the ThinPrep® system in 1996, invasive cervical cancers in the US have declined. However, there remains an ongoing need for cervical screening. While the application of warm water on the collection speculum has the least risk to the quality of a collected Pap sample, many clinicians still employ the use of a lubricant gel on the speculum to ease patient discomfort during a pelvic exam. Unfortunately, the use of such lubricants during sample collection for the ThinPrep® Pap test, particularly lubricants having carbomer-based formulations, may adversely affect specimen slide adequacy, and can elevate "Unsatisfactory for Evaluation" (hereinafter "UNSAT") rates for laboratories.

SUMMARY

In accordance with one aspect of the disclosed inventions, a method for processing a cytological specimen that is (or is believed to be) contaminated by a lubricant includes the acts of pelletizing the specimen and decanting (i.e., removing) the original ("collection") preservative solution; adding a wash solution to the pelleted specimen; centrifuging the specimen and wash solution to form a supernatant and cell pellet; decanting the supernatant; and then re-suspending the cellular matter in a replacement preservative solution. The resulting (re-processed) specimen may then be used to make a specimen slide, e.g., using a ThinPrep® instrument. In one embodiment, the wash solution is a Tris-based alkaline buffer solution prepared in methanol (i.e., 20% methanol). The method may also include adding a salt (e.g., NaCl or CytoLyt® salts) to the preservative solution containing the washed, re-suspended cells. The wash solution may further comprise a proton-rich protein and/or a basic amino acid, such as arginine, lysine, or guanidine.

In one embodiment, the method for processing a cytological specimen includes adding a salt (such as NaCl or CytoLyt salts) to the specimen in the original ("collection") preservative solution; and thereafter preparing a microscope slide having cells from the specimen. This embodiment of the method may further include, before the step of adding the salt, performing a wash with a Tris-based alkaline buffer solution. Performing the wash may include adding the Tris-based alkaline buffer solution to the (pelleted/decanted) specimen; centrifuging the specimen and buffer solution to form a supernatant and cell pellet; decanting the supernatant; and re-suspending the cellular matter in a preservative solution. The buffer solution may include a proton-rich protein and/or a basic amino acid, such as arginine, lysine, or guanidine.

In accordance with another aspect of the disclosed inventions, a wash solution provided for remediating a cytological specimen contaminated with lubricant comprises a Tris-based alkaline buffer prepared in methanol. The buffer may be prepared in 20% methanol. The wash solution may further include a proton-rich protein and/or a basic amino acid, such as arginine, lysine, or guanidine.

Additional embodiments, as well as aspects, features and advantages, of the disclosed inventions are set forth in part in the detailed description which follows, and in part will be inherent or otherwise obvious from the description or may be learned by practice of the disclosed embodiments. In the following detailed description, reference is made to the accompanying drawings which form a part thereof and in which is shown by way of illustration of various embodiments for practicing the disclosed inventions. The embodiments will be described in sufficient detail to enable those skilled in the art to practice the disclosed inventions, and it is to be understood that other embodiments may be utilized and that structural changes may be made without departing from the scope of the disclosed inventions. The following detailed description is, therefore, not to be taken in a limiting sense, and the scope of the disclosed inventions is defined solely by the appended claims and their legal equivalents.

BRIEF DESCRIPTION OF THE DRAWINGS

The above and other aspects and features of the disclosed embodiments will become more apparent upon consideration of the ensuing detailed description, taken in conjunction with the accompanying drawings, in which like reference characters refer to like parts throughout, and in which.

DETAILED DESCRIPTION OF THE ILLUSTRATED EMBODIMENTS

The disclosure is described below primarily in the context of a wash solution and method for remediating lubricant contamination in cytological specimens. The source of lubricant contamination for gynecological specimens may occur at the point of specimen collection or from personal use. Clinicians may apply lubricant to the speculum during a gynecological exam to ease patient discomfort during sample collection. For the same reason, lubricant is frequently used in non-gynecological applications such as cystoscopy, collection of lavages or bladder washes, as well as any type of superficial brushings that necessitate the use of a scope. Another source of lubricant contamination for non-gynecological sampling can be from the use of ultrasound gel that is spread onto the skin prior to the collection of a fine needle aspiration specimen.

Lubricant contamination, especially with lubricants that contain carbomer, is a problem for specimens because the lubricant can occlude the filter during slide preparation on the ThinPrep® processor, preventing adequate collection of cells, and/or impeding cell transfer. This may result in an UNSAT slide result, in which case the cytotechnologist and cytopathologist are unable to make a diagnosis of the contaminated patient sample. An UNSAT slide result requires that the patient be called back for providing a new sample.

Figure 1:
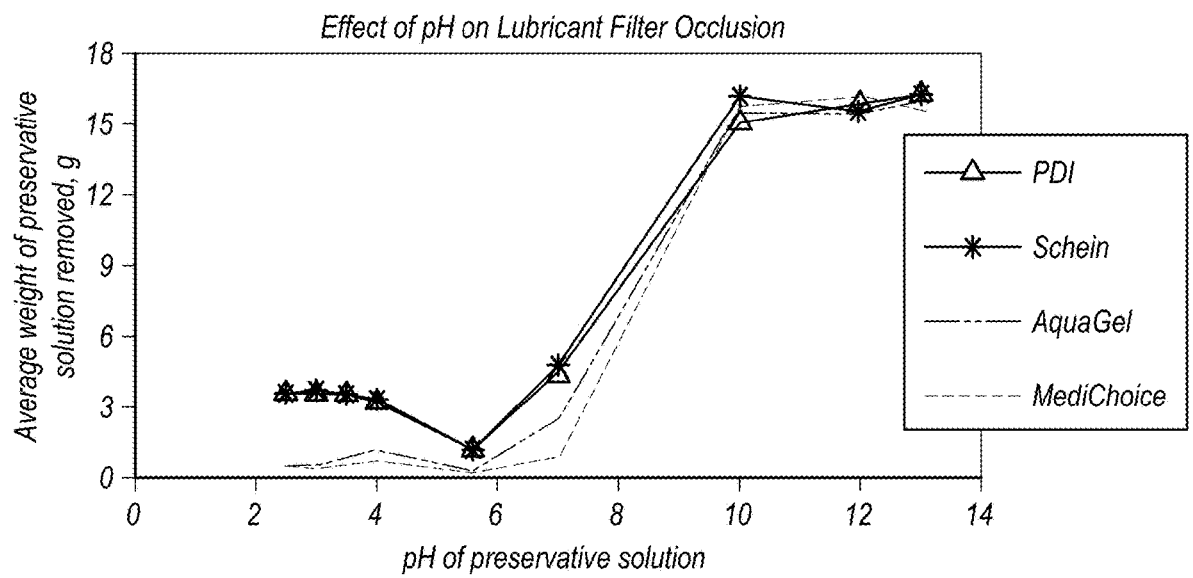
FIG. 1 is a graph showing the effect of pH on lubricant filter occlusion.

The wash solution for remediating specimens contaminated with lubricant preferably has an alkaline pH. The effect of pH on filter occlusion with several carbomer-containing lubricants commonly used in clinical practice is shown in FIG. 1. A decrease in the average weight of preservative solution removed (shown along the y-axis in FIG. 1) indicates increased filter membrane occlusion. Typical preservative solutions, such as PreservCyt® and CytoLyt® solutions (both made and sold by Hologic), have relatively low pH values, i.e., 5.7 and 7.1, respectively. As shown in FIG. 1, the carbomer-containing lubricants would have high filter occlusion properties in typical preservative solutions (e.g., at a pH of 5.7 or 7.1). The filter membrane occlusion properties of the lubricants can be reduced when the lubricants are exposed to a high pH, as demonstrated in FIG. 1.

Figure 2:
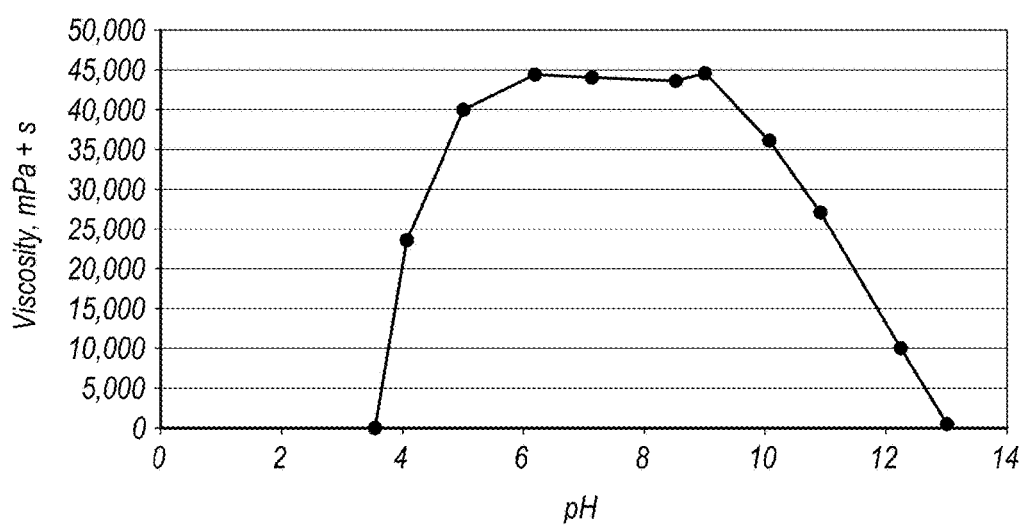
FIG. 2 is a graph of pH versus viscosity for a carbomer-based lubricant.
Figure 3A:
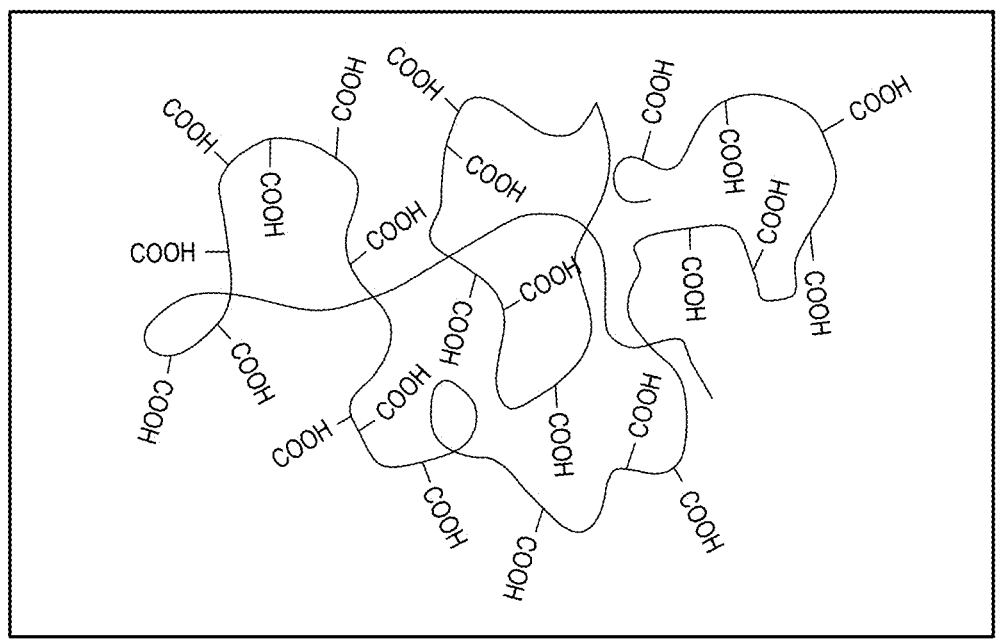
FIGS. 3a and 3b depict molecules of carbomer-based lubricants at a neutral pH and a basic pH, respectively.
Figure 3B:
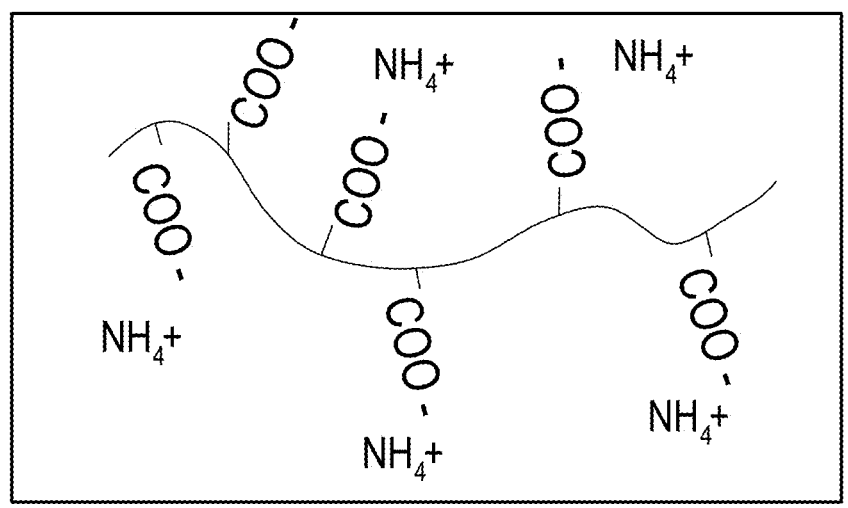

This may be due to the effect the pH has on the viscosity of the lubricant. FIG. 2 shows that elevated pH has an inverse effect on viscosity for carbomer-based lubricants. Specifically, the graph in FIG. 2 shows viscosity versus pH for Carbopol® EZ-2 polymer (Lubrizol Corp.). At neutral pH, carbomer-based lubricants are in a viscous state, as shown in FIG. 3a. At a higher, basic pH, the carbomer becomes de-protonated to yield a more charged molecule in a linear orientation, and thus a less viscous state, as shown in FIG. 3b. As demonstrated in FIG. 1, this lower viscosity at an alkaline state decreases filter occlusion, as evidenced by the increased preservative solution removal.

As such, in one embodiment, the wash solution is a Tris-based buffer of alkaline pH. The wash solution may be prepared in a methanol/water solution. For example, the Tris-based alkaline buffer may be prepared in 20% methanol.

However, while the increased pH resulted in improved cell collection and transfer, lubricant was still present, appeared to be associated directly with the surface of cells, and impeded visual observation of cell morphology. Therefore, the wash solution may also contain a concentration of a proton-rich protein such as protamine, and/or basic amino acids such as arginine, lysine, or guanidine. The presence of these compounds is intended to interrupt the association between the charged copolymer and cell surface proteins by providing an alternative association partner via electrostatic interaction. For example, the net positive charge of arginine at basic pH can help buffer between the carbomer and cell surfaces in a way that prevents clumping (an issue commonly observed in clinical samples contaminated with lubricant), while maintaining a low carbomer viscosity.

As such, a Tris-based alkaline buffer wash solution prepared in 20% methanol may be used to remediate lubricant contamination of ThinPrep® specimens. The wash solution may further include a concentration of a proton-rich protein such as protamine, and/or basic amino acids such as arginine, lysine, or guanidine. The occlusion properties of the lubricant may be diminished and cell collection onto the slide may be improved by using this wash solution.

Figure 4:
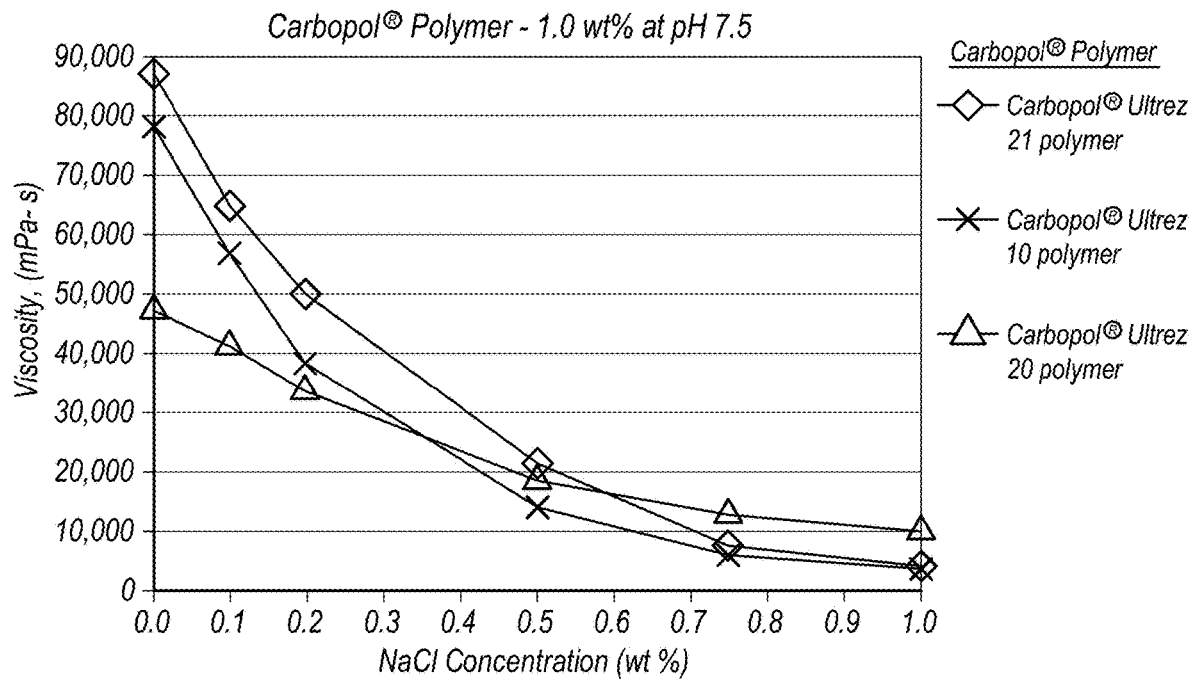
FIG. 4 is a graph of salt concentration versus viscosity for carbomer-based lubricants.

In one embodiment, salt solution is added to the final specimen after performing the wash. This may be a solution of NaCl or CytoLyt® salts. The addition of salt directly to a sample contaminated with lubricant has been shown to reduce the filter occlusion properties of the lubricant and improve cell transfer. Carbomer polymers have a low ion tolerance and therefore viscosity can be controlled by ionic strength. FIG. 4 depicts the effect of salt on Carbopol® polymer gel viscosities. As shown in FIG. 4, viscosity decreases with increased salt concentration.

Figure 5:
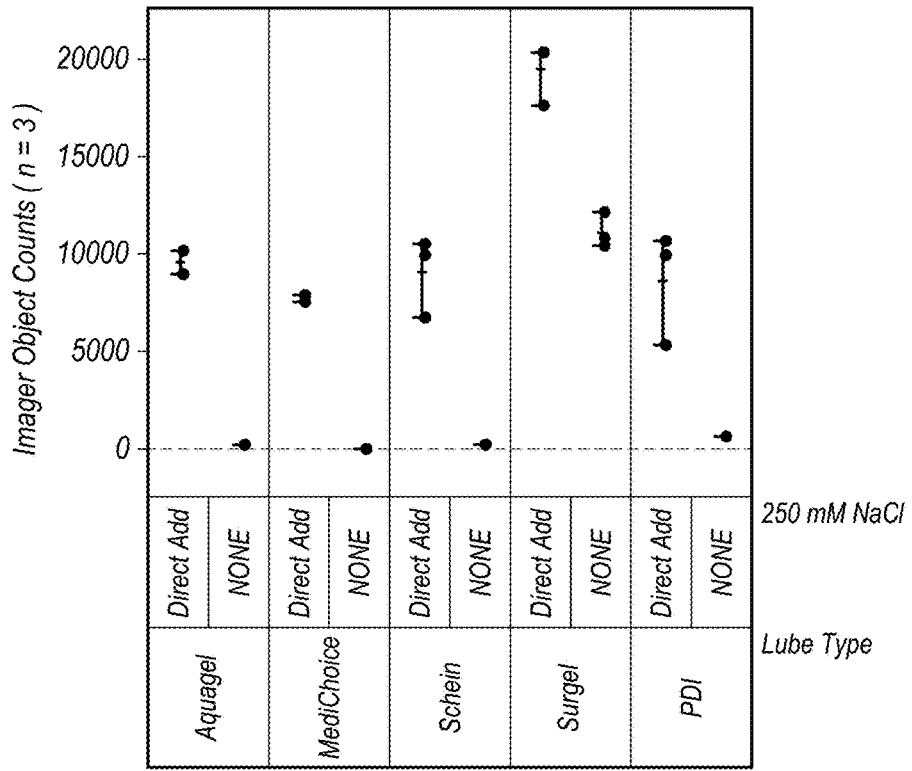
FIG. 5 is a table showing the effect on cell transfer that adding salt has on a specimen contaminated with lubricant.
Figure 6:
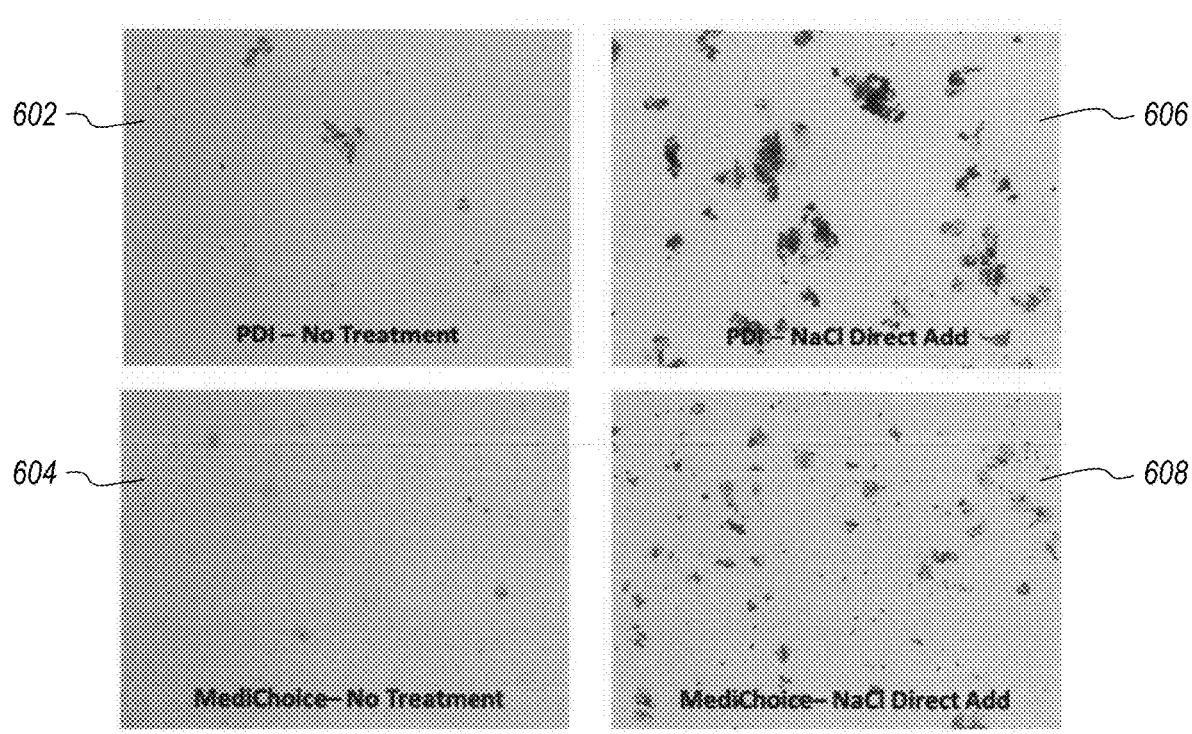
FIG. 6 depicts images of microscope slides prepared from specimens contaminated with lubricants, wherein the images on the left have not been treated, and the images on the right have been treated with salt.

In another embodiment, a specimen contaminated with lubricant can be remediated by adding salt solution to the specimen without performing the wash. As shown in FIG. 5, adding salt solution directly to samples containing different lubricants increases the number of objects that are transferred to the slide. The samples that were not treated at all (shown in the columns labeled "NONE" in FIG. 5) had very few, if any, objects transfer to the slide. FIG. 6 depicts samples prepared from cell pools spiked with lubricants, where the images 602, 604 on the left have not been treated, and the images on the right 606, 608 have been treated with salt. The specimens that have not been treated have very few objects on the slide, while the specimens that have been treated with salt have many more objects on the slides. As such, adding salt solution to the specimen without performing the wash may be effective for remediating a sample contaminated with lubricant.

Figures 7, 8, 9:
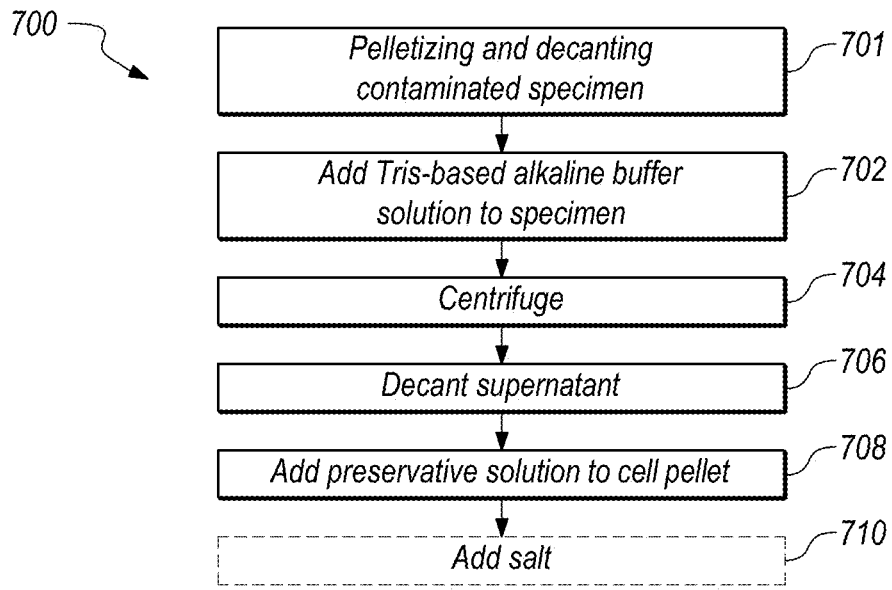
FIG. 7 is a flow chart of a method for processing a cytological specimen that is contaminated with lubricant.
FIG. 8 is a table showing the number of slides prepared from lubricant contaminated samples with image object counts of at least 5000, with and without the embodied treatment.
FIG. 9 is a table showing "unsatisfactory for evaluation" rates of slides prepared from lubricant contaminated specimens, with and without the embodied treatment.

A procedure 700 for making a specimen slide from a patient sample that is contaminated (or believed to be potentially contaminated) with a lubricant is shown in FIG. 7. While the procedure is described as a series of steps performed in succession, the term "step" is used for convenience, and the underlying acts being described are not necessarily performed as "steps" as this term is used in 35 U.S.C. § 112. Because the patient sample is initially contained in the original collection preservative solution (aka PreservCyt solution), in the first step 701 of the procedure, the specimen is pelleted by centrifugation and the preservation solution is decanted, leaving only the pelleted cellular matter, including any solidified lubricant, in the sample container. Then, in step 702, a Tris-based alkaline buffer solution is added to the pelleted specimen. Next, in step 704, the specimen in the wash solution is centrifuged to form a supernatant and a cell pellet. Next, in step 706, the supernatant is decanted. Finally, in step 708, the cell pellet is re-suspended in a replacement preservative solution and a specimen slide may then be successfully produced, e.g., using a ThinPrep® instrument. Optionally, in step 710, a salt may be added to the re-suspended cell pellet in the replacement preservative solution.

As discussed above, in one embodiment, the method may include performing only the step 710 of adding salt solution, and may not include steps 702-708. In this embodiment, the specimen suspended in preservative solution is provided, and salt is added to the preservative solution containing the specimen. A microscope slide is prepared using, for example, the ThinPrep® system. Due to the salt treatment, which reduces the occlusion properties of the lubricant, the microscope slide would likely have enough cells from the specimen to be satisfactory for evaluation.

The procedure 700 for performing the wash and/or adding the salt solution may be performed after a specimen has already been determined to be UNSAT. In other words, the specimen is processed and a slide is formed using the ThinPrep® system, and the slide prepared from the specimen is determined to be UNSAT. Such a specimen may be contaminated with lubricant. As such, the wash solution and/or salt solution may be used to remediate the specimen in its original collection preservative solution, as described above, and a new slide may be prepared from the treated specimen. Alternatively, the specimen may be treated with the wash solution and/or the salt solution before any slides are prepared from the specimen.

The effectiveness of this remediation technique on reducing adverse effects of lubricant contamination has been tested on an eight-member panel of lubricants that may cause UNSAT issues for the ThinPrep® Pap Test. Three cell pools, prepared from ThinPrep® specimens identified as either NILM, LSIL, or atrophic, were used in this study. The cell pools were dispensed into individual vials at concentrations of moderate cellularity. The vials were then spiked with the lubricants at levels sufficient to generate an UNSAT upon slide preparation on a ThinPrep® processor. Up to six replicates were reprocessed for each lubricant and cell pool using the buffered, Tris-based wash solution. The slides were prepared on a ThinPrep® processor, stained with the ThinPrep® Pap Stain, and coverslipped. A second slide was then prepared from each residual sample vial after adding an aliquot of solution containing CytoLyt® salts, and then stained and coverslipped.

All the slides were run on the ThinPrep® imaging system, and the imaging slide metrics were collected to retrieve object counts. Object count data were collected using an imaging quality control test procedure. This is an automated software tool that records the number of dark, round objects (ostensibly nuclei) identified by the image segmentation phase of the ThinPrep® imager algorithm.

Slides from approximately half of the sample replicates were reviewed by ASCP certified Cytotechnologists (CTs) for cellular adequacy. Adequacy was determined by taking the average of all well-preserved and well-visualized squamous cells found in ten alternating fields of view (FOVs) at 40× magnification using a field number (FN) 22 eyepiece. The FOV were counted along the diameter and included the center of the cell spot. Slides were identified as Satisfactory (SAT), SAT-Borderline, UNSAT-Borderline, or UNSAT.

The slides that generated object counts on the imager, arranged by cell pool type and treatment condition, are shown in FIG. 8. A total of 223 slides were reviewed by CTs for a SAT or UNSAT determination. An UNSAT was defined as fewer than 5,000 cells, or less than an average of 3.8 cells/FOV, regardless of whether abnormal cells are present.

Slides prepared from cell pools spiked with the lubricants showed an increase in cell coverage when the wash method was utilized and converted from UNSAT to satisfactory. As shown in FIG. 9, the Satisfactory for Evaluation (SAT) rate went from 8.9% (i.e., 91.1% UNSAT) without treatment to 38.9% (i.e., 61.1% UNSAT) when washed with the Tris-based alkaline buffer. The SAT rate increased to 98.6% (i.e., 1.4% UNSAT) with the use of the wash buffer combined with the addition of the CytoLyt® salts, as shown in FIG. 9.

For many lubricants, a very minimal amount in the ThinPrep® vial can be a detriment to cell transfer and create an UNSAT result. This wash solution, combined with an addition of CytoLyt® salts to the final vial, may help reduce UNSAT rates in laboratories that receive ThinPrep® specimens contaminated with lubricant. In another embodiment, the wash solution alone may help reduce UNSAT rates in laboratories that receive ThinPrep® specimens contaminated with lubricant. In yet another embodiment, the addition of salts to the final vial without using the wash solution may help reduce UNSAT rates in laboratories that receive ThinPrep® specimens contaminated with lubricant.

Although this disclosure has been provided in the context of certain embodiments and examples, it will be understood by those skilled in the art that the disclosure extends beyond the specifically disclosed embodiments to other alternative embodiments and/or uses of the embodiments and obvious modifications and equivalents thereof. Additionally, the skilled artisan will recognize that any of the above-described methods can be carried out using any appropriate apparatus. Further, the disclosure herein of any particular feature, aspect, method, property, characteristic, quality, attribute, element, or the like in connection with an embodiment can be used in all other embodiments set forth herein. Thus, it is intended that the scope of the present inventions disclosed herein should not be limited to the illustrated and/or described embodiments, but are instead defined only by the claims appended hereto, and their legal equivalents.

What is claimed is:

1. A method for removing lubricant contamination from a cytological specimen sample suspended in a collection preservative solution, the method comprising:

pelletizing the specimen;

decanting the collection preservative solution to isolate the pelleted specimen;

adding a wash solution to the pelleted specimen, wherein the wash solution comprises a Tris-based alkaline buffer and a basic amino acid;

centrifuging the specimen and wash solution to form a supernatant and cell pellet;

decanting the supernatant to isolate the cell pellet; and adding a replacement preservative solution to the cell pellet.

2. The method of claim 1, wherein the buffer is prepared in methanol.

3. The method of claim 2, wherein the buffer is prepared in 20% methanol.

4. The method of claim 1, further comprising adding a salt to the replacement preservative solution and cell pellet.

5. The method of claim 4, wherein the salt comprises NaCl.

6. The method of claim 1, wherein the basic amino acid comprises arginine or lysine.

7. The method of claim 4, wherein adding the salt comprises adding a preservative solution that comprises salt.

8. The method of claim 1, wherein the wash solution further comprises guanidine.

\* \* \* \* \*